United States Patent
Daniel (10) Patent No.: US 11,565,479 B2
(45) Date of Patent: Jan. 31, 2023

(54) METHOD FOR CONNECTING A FIRST COMPONENT TO A SECOND COMPONENT

(71) Applicant: Gerresheimer Regensburg GmbH, Regensburg (DE)

(72) Inventor: Christian Daniel, Wernberg-Köblitz (DE)

(73) Assignee: Gerresheimer Regensburg GmbH, Regendsburg (DE)

( * ) Notice: Subject to any disclaimer, the term of this patent is extended or adjusted under 35 U.S.C. 154(b) by 26 days.

(21) Appl. No.: 16/839,030

(22) Filed: Apr. 2, 2020

(65) Prior Publication Data
US 2020/0316315 A1 Oct. 8, 2020

(30) Foreign Application Priority Data
Apr. 2, 2019 (DE) .................... 10 2019 108 583.7

(51) Int. Cl.
*B29C 65/00* (2006.01)
*B29C 65/02* (2006.01)
(Continued)

(52) U.S. Cl.
CPC ............. *B29C 65/02* (2013.01); *A61M 5/343* (2013.01); *A61M 5/349* (2013.01); *B29C 65/52* (2013.01);
(Continued)

(58) Field of Classification Search
CPC .. A61M 5/343; A61M 5/349; A61M 2207/00; B29C 65/48; B29C 65/4855;
(Continued)

(56) References Cited

U.S. PATENT DOCUMENTS 3,278,357 A * 10/1966 Gettig .................. A61M 5/349
156/294
3,390,678 A * 7/1968 Lewis .................. A61M 5/343
604/240
(Continued)

FOREIGN PATENT DOCUMENTS

CN 102666761 9/2012
DE 198 80 965 7/1999
(Continued)

OTHER PUBLICATIONS

Extended European Search Report dated Jun. 16, 2020, in European Patent Application No. 20165802.8, 3 pages.
(Continued)

*Primary Examiner* — William R Carpenter
(74) *Attorney, Agent, or Firm* — Lowe Graham Jones PLLC (57) ABSTRACT

The invention relates to a method for connecting a first component, in particular a lancing means, to a second component, in particular a syringe body, in order to produce a product for medical or cosmetic purposes, by means of adhesion, having the following steps: (a) providing the first and the second component; (b) tempering at least one first contact surface of the first component and/or at least one second contact surface of the second component to a temperature T1; and (c) applying an adhesive to at least one portion of the first contact surface and/or to at least one portion of the second contact surface, wherein the adhesive is at a temperature T2, wherein temperatures T1 and T2 differ only by a tolerance deviation, wherein the tolerance deviation is at most 10° C.

12 Claims, 4 Drawing Sheets

(51) Int. Cl.
*A61M 5/34* (2006.01)
*B29C 65/52* (2006.01)
(52) U.S. Cl.
CPC . *A61M 2205/3368* (2013.01); *A61M 2207/00* (2013.01); *A61M 2207/10* (2013.01)
(58) Field of Classification Search
CPC ....... B29C 65/40; B29C 65/405; B29C 65/42; B29C 65/425
See application file for complete search history.

(56) References Cited

U.S. PATENT DOCUMENTS

| | | | | |
|---|---|---|---|---|
| 3,470,604 | A * | 10/1969 | Zenick | B29C 66/131 29/447 |
| 3,635,875 | A * | 1/1972 | Wesch | C08G 59/226 523/428 |
| 2002/0138042 | A1 * | 9/2002 | Llorach | A61M 5/343 422/26 |
| 2009/0209919 | A1 * | 8/2009 | Sakurai | A61M 5/284 528/421 |
| 2012/0010573 | A1 * | 1/2012 | Lundquist | B29C 45/14311 604/192 |
| 2013/0231617 | A1 * | 9/2013 | Hoppe | A61M 5/34 156/272.8 |
| 2014/0236102 | A1 * | 8/2014 | Matsumoto | A61M 5/344 604/272 |
| 2015/0100022 | A1 * | 4/2015 | Vedrine | A61M 5/343 604/117 |
| 2019/0023602 | A1 * | 1/2019 | Baumann | C03B 23/0496 |

FOREIGN PATENT DOCUMENTS

| | | |
|---|---|---|
| DE | 10 2010 045 095 | 3/2012 |
| GB | 1 215 435 | 12/1970 |

OTHER PUBLICATIONS

First Office Action dated Oct. 9, 2021 (with English translation), in Chinese Patent Application No. 202010253862.0, 22 pages.
Second Office Action dated Apr. 25, 2022 (with English summary), in Chinese Patent Application No. 202010253862.0, 17 pages.

* cited by examiner

METHOD FOR CONNECTING A FIRST COMPONENT TO A SECOND COMPONENT

PRIORITY CLAIM

This application claims the benefit of priority from Germany Patent Application No. 10 2019 108 583.7, filed Apr. 2, 2019, the contents of which are incorporated herein by reference in their entirety.

FIELD OF THE INVENTION

The invention relates to a method for connecting a first component, in particular a lancing means, to a second component, in particular a syringe body, by means of adhesion.

BACKGROUND OF THE INVENTION

It is often desirable for syringes to be supplied with a lancing means, for example a needle or a cannula. Pre-filled syringes in particular are preferably supplied with a lancing means. The pre-filled syringes (syringe bodies), which can be made of glass or plastic, are manufactured, packaged, sterilized and made ready for filling directly in the bottler's clean room by the primary packaging manufacturer. They can then be used for filling without any further treatment steps. The pre-filled syringes are filled by the filler from the proximal side or the flange side.

The lancing means is usually fastened with an adhesive in the syringe, or in a lancing means channel in the distal end section of the syringe. A lancing means can be a needle, a cannula, or a similar device. The difficulty lies in adequately wetting the corresponding contact surfaces of the lancing means and the syringe body with the adhesive. To ensure this, the lancing means channel is designed with a larger diameter. However, a lancing means channel of this size also requires a larger amount of adhesive in order to fill it. This entails additional financial expenditure. A lancing means channel with a larger diameter also harbors the risk that the adhesive gets into the reservoir for the medium. With some drugs or vaccines, contact with the adhesive can lead to unwanted interactions that can render the substance unusable. Furthermore, an excessively large diameter of the lancing means channel can lead to the holding forces of the adhesive not being sufficient. The specified requirements for corresponding pulling forces can therefore not be met.

The use of very low-viscosity adhesives is also disadvantageous, since they tend to form droplets, which makes handling these adhesives difficult. There is also a risk in this case that the adhesive will pass through the lancing means channel and get into the reservoir.

The problems mentioned at the outset with regard to the bonding of a lancing means in a syringe body can also be transferred to similarly arranged arrangements or bonding of other first components in corresponding receiving volumes of the second component.

An important goal of the present invention is accordingly to provide a method by means of which the disadvantages mentioned above can be overcome.

SUMMARY OF THE INVENTION

The present invention is directed to a method for connecting a first component, in particular a lancing means, to a second component, in particular a syringe body, in order to produce a product for medical or cosmetic purposes, by means of adhesion, having the following steps: (a) providing the first and the second component; (b) tempering at least one first contact surface of the first component and/or at least one second contact surface of the second component to a temperature $T1$; and (c) applying an adhesive to at least one portion of the first contact surface and/or to at least one portion of the second contact surface, the adhesive having a temperature $T2$, temperatures $T1$ and $T2$ differing only by a tolerance deviation, and the tolerance deviation being at most 10° C.

The term "adhesive" or "adhesive agent" is understood herein to mean a non-metallic material that connects components to one another by adhesion (surface adhesion) and cohesion (internal strength). The cross-section of an adhesive bond can advantageously be subdivided into an adhesion zone and a cohesion zone. In the adhesion zone, the adhesive changes its chemical structure and composition due to the adhesion to the contact surface. This also changes the macroscopic properties of the adhesive. The adhesive is in its unchanged state in the cohesion zone. The adhesive is advantageously an organic adhesive. The adhesive can preferably be a one-component or a two-component adhesive.

The viscosity of adhesives is usually dependent on the temperature. According to the invention, the adhesive is therefore at a temperature $T2$ at which the adhesive also has the required viscosity. This required viscosity is preferably designed such that the corresponding contact surface is adequately wetted. On the other hand, the required viscosity is not so low, that is, the adhesive is so flowable that areas adjoining the contact surface come into undesirable contact with the adhesive. The viscosity of the adhesive can therefore be controlled by tempering the adhesive according to the invention. The viscosity of the adhesive could thus preferably be reduced by heating the adhesive.

The method according to the invention also has the advantage that at least the contact surfaces of the first and second component are tempered before the adhesive is applied, so that the temperature $T1$ of the first and/or the second contact surface differs from the temperature $T2$ of the adhesive only by a tolerance deviation.

If temperatures $T1$ and $T2$ differ from each other by more than the tolerance deviation, contact of the adhesive with the contact surface(s) results in a non-insignificant temperature compensation, which results in a non-negligible change in the viscosity of the adhesive. A tempering of the first and/or second contact surface to a temperature $T1$, which corresponds to temperature $T2$ within the tolerance deviation, accordingly prevents a non-negligible change in the temperature of the adhesive. This also prevents a non-negligible change in viscosity. The required viscosity of the adhesive can thus be reliably set by tempering the adhesive, and an impairment of the viscosity due to the different temperature of the contact surfaces will be excluded.

The method can preferably comprise a tempering step by means of which the adhesive is brought to temperature $T2$. This tempering step is preferably carried out before step (c) or step (b).

Alternatively, it would be possible for a specific supply of adhesive to be kept permanently at temperature $T2$. When several products are being manufactured, a predetermined amount of adhesive is preferably removed for each individual product. This amount of adhesive therefore is at temperature $T2$ and thus the desired viscosity. An explicit tempering step for the adhesive would therefore no longer be necessary.

Before step (c), i.e., the application of the adhesive, a control measurement of temperature $T2$ could advantageously be carried out by means of a temperature measuring device. Such a temperature measuring device can, for example, carry out a contactless temperature measurement. Such temperature measuring devices are, for example, laser temperature measuring devices or infrared temperature measuring devices. Alternatively, the temperature measuring device can have a temperature sensor, which is arranged in the (immediate) vicinity of the adhesive. The temperature measuring device measures the temperature TM and forwards this value to a preferred control device. This preferred control device compares the measured temperature TM with the predetermined temperature T2. In the event of a deviation which lies outside a predetermined tolerance value, the control device controls a corresponding adhesive tempering device, as a result of which the temperature T2 is regulated.

A "contact surface" is to be understood as meaning those surfaces which are to come into contact with the adhesive or those surfaces to which the adhesive is to be applied. According to step (c), the adhesive can first be applied to at least one portion of the first contact surface and/or to at least one portion of the second contact surface.

When applying the adhesive in portions, it can be advantageous if the adhesive is distributed over the entire first or second contact surface in a further step. Such distribution of the adhesive can take place in a wide variety of ways, for example by mechanical means, by changing the position of one component or both components relative to one another or by changing the volume of a receiving volume in which the adhesive is located. Furthermore, the adhesive can be distributed on the contact surface by flowing along the contact surface, for example due to a force, for example due to gravitational force.

In step (c), the adhesive can advantageously be applied to the entire first contact surface and/or the entire second contact surface.

An optimal adhesive connection between the first and the second component exists when the first and the second contact surface are completely covered with the adhesive. With such an optimal adhesive connection, the adhesive connection can withstand the specified pull-out or pull-off forces between the two components.

According to a preferred embodiment, the tempering in step (b) is heating. According to a further preferred embodiment, the tempering in step (b) is cooling.

According to the invention, in step (b) at least the first and/or at least the second contact surface is tempered, so that these contact surfaces are at a temperature T1 which corresponds to the temperature T2 within the tolerance deviation. Such tempering can preferably be carried out either directly or indirectly. In the case of direct tempering, a tempering medium preferably touches the at least one first contact surface and/or the at least one second contact surface.

In the case of indirect tempering, a tempering medium advantageously touches a tempering area of the first component and/or the second component, the tempering area of the first component and/or the second component comprising, surrounding or being arranged in the immediate vicinity of this contact surface. In the case of indirect tempering, a tempering medium advantageously touches a tempering surface of the tempering area which does not correspond to the contact surface. Advantageously, there is a heat flow from the tempering surface through the tempering area to the corresponding contact surface or a heat flow from the corresponding contact surface to the tempering surface. The direction of the heat flow determines whether the corresponding contact surface is heated or cooled. The contact surface can thus be brought to temperature T1. If, for example, the corresponding contact surface lies within the first or the second component, for example in a receiving volume, the tempering surface could be an outer surface of the corresponding component, which is in close proximity to the internal contact surface. Due to an advantageous thermal conductivity of the material in the tempering area, heat impingement takes place between the contact surface and the tempering surface after the tempering medium touches the tempering surface and the tempering surface is tempered.

It would also be conceivable for the entire first or second component to be tempered. This is particularly advantageous if the corresponding component is comparatively small.

According to a preferred embodiment, the temperature T1 of the first contact surface and/or the temperature T1 of the second contact surface is monitored by a temperature measuring device. Such a temperature measuring device can, for example, carry out a contactless temperature measurement. Such temperature measuring devices are, for example, laser temperature measuring devices or infrared temperature measuring devices. Alternatively, the temperature measuring device can have a temperature sensor which is arranged on or in the immediate vicinity of the first and/or second contact surface.

The temperature measuring device advantageously measures a temperature value TM2 of the first contact surface and/or the second contact surface. This temperature value is transmitted to a preferred control device. This preferred control device compares the measured temperature TM with the predetermined temperature T2. In the event of a deviation which lies outside a predetermined tolerance value, the control device controls a corresponding tempering device, as a result of which the temperature T2 is regulated.

According to a preferred embodiment, the second component comprises a receiving volume, which is delimited, at least in portions, by the second contact surface. The first component can preferably be arranged in portions in the receiving volume. When the first component is arranged in the receiving volume, the first and the second contact surfaces are advantageously opposite one another. It is furthermore advantageous if an adhesive cavity is formed at least in portions between the contact surfaces when the first component is arranged in the receiving volume. The first component is advantageously cylindrical, preferably circular-cylindrical. The contact surface advantageously corresponds, at least in portions, to an outer surface, which preferably completely spans the first component. In addition, it is advantageous that the receiving volume is cylindrical, preferably circular-cylindrical. The contact surface of the second component is thus preferably an inner surface, which preferably completely surrounds or delimits the receiving volume. The first component is advantageously inserted centrally into the receiving volume, so that the distance between the first and the second contact surface is constant in the circumferential direction. The adhesive cavity is advantageously delimited in the circumferential direction by the first and the second contact surface. The adhesive is preferably introduced into the adhesive cavity so that the latter is completely filled with the adhesive. This advantageously creates an adhesive bond between the first and the second contact surfaces.

According to a preferred embodiment, after step (b), the first component is introduced into the receiving volume of the second component at least in portions. It is in this case advantageous that, in step (c), the adhesive is applied to the entire first contact surface and the entire second contact surface by filling the adhesive cavity with adhesive. The adhesive cavity is advantageously oriented such that it has an upper opening which lies in the vertical direction above a lower opening or a lower wall. Accordingly, it is advantageous for the adhesive to be introduced into the adhesive cavity through the upper opening. Thus, among other things, gravity advantageously acts on the adhesive. The adhesive therefore sinks down and thus fills the adhesive cavity. Embodiments would also be conceivable in which, alternatively or in addition to the gravitational force, a capillary force acts on the adhesive, as a result of which it penetrates into the adhesive cavity. Since the viscosity of the adhesive can be matched to the dimensions of the adhesive cavity by tempering the adhesive to temperature $T2$, a viscosity can be set by means of which the adhesive can penetrate into the adhesive cavity and fill it completely.

Advantageously, step (c) takes place immediately after the first component has been introduced into the receiving volume of the second component. This ensures that the first tempered contact surface and/or the tempered second contact surface are at a temperature which is still within the tolerance deviation. A possible external temperature influence, i.e., a possible cooling (or heating) of the contact surfaces can thus be disregarded.

According to a preferred embodiment, after step (c), the first component is introduced into the receiving volume of the second component at least in portions. In step (c), the adhesive is advantageously applied to at least one portion of the first contact surface or to at least one portion of the second contact surface. In step (c), the adhesive is preferably applied to at least one portion of the second contact surface by the adhesive being introduced into the receiving volume. The amount of adhesive applied is advantageously measured such that the adhesive cavity is filled. Accordingly, adhesive is applied to the entire first and the entire second contact surface after the first component has been inserted in portions into the receiving volume of the second component. A certain amount of adhesive can thus be applied in (the receiving volume) or on the first and/or second component. By bringing the first and the second component together in a preferable manner, the adhesive is distributed over the entire first and second contact surfaces. By reducing the volume of the receiving volume due to the introduction of the first component into the second component, the adhesive is preferably distributed over all of the contact surfaces.

Advantageously, the application of the adhesive and the introduction or the bringing together of the first and the second component takes place within a period of time within which a possible external temperature influence, i.e., a possible cooling (or heating) of the contact surfaces can be disregarded, so that temperature $T1$ continues to lie within the tolerance deviation of $T2$.

According to a preferred embodiment, temperature $T2$ is greater than room temperature. Temperature $T2$ is accordingly preferably greater than 20° C., preferably greater than 25° C. The adhesive is therefore preferably heated, whereby the viscosity of the adhesive is reduced accordingly. Typically, the first and the second component are at room temperature, i.e., approximately 20° C., before step (b). Without the tempering according to step (b), the temperature compensation upon contact of the adhesive with the contact surfaces would accordingly decrease the adhesive temperature $T1$, as a result of which the viscosity of the adhesive increases. Such a higher viscosity would, for example, no longer be able to penetrate sufficiently into the preferred adhesive cavity. Thus, the preferred adhesive cavity would not be adequately filled with adhesive, whereby an insufficient adhesive connection is formed between the first and the second contact surface. Such an inadequate adhesive connection can result in the adhesive connection withstanding only insufficiently low pull-out forces of the first component from the receiving volume of the second component.

According to a further preferred embodiment, temperature $T1$ deviates from temperature $T2$ by at most 5° C. Temperature $T1$ preferably deviates from temperature $T2$ by at most 4° C. More preferably, temperature $T1$ deviates from temperature $T2$ by at most 3° C. More preferably, temperature $T1$ deviates from temperature $T2$ by at most 1.5° C.

According to a further preferred embodiment, the first contact surface is pretreated and/or activated before step (c). This pretreatment of the first contact surface is preferably selected from the group including cleaning, mechanical pretreatment, chemical pretreatment, thermal pretreatment, and physical pretreatment. It is also advantageous that the second contact surface is pretreated and/or activated before step (c). The pre-treatment of the second contact surface is preferably selected from the group including cleaning, mechanical pretreatment, chemical pretreatment, thermal pretreatment, and physical pretreatment.

A suitable advantageous pretreatment is intended to apply possible adhesion-reducing layers to the contact surfaces. Such layers are present on the base material and can be, for example, impurities, absorbent media or oxide layers. Such layers should advantageously be removed by a suitable pretreatment. The choice of pretreatment depends on the base material and the expected anti-adhesion layers.

A preferred cleaning can be done, for example, by washing the contact surfaces, for example with distilled water, solvents or compressed air. A preferred mechanical pretreatment can be carried out, for example, by grinding, sanding, brushing, or $CO2$ irradiation. A preferred chemical pretreatment can be carried out, for example, by pickling with acidic or alkaline solutions. A preferred thermal pretreatment can be carried out, for example, by flame treatment. A preferred electrochemical pretreatment can be carried out, for example, by phosphating or chromating. A preferred physical pretreatment can be carried out, for example, by atmospheric plasma treatment, low-pressure plasma discharge, corona discharge, UV treatment or laser treatment.

Furthermore, it can be advantageous for the first and/or the second contact surface to be activated before the adhesive is applied. Activation is a modification of the contact surface so that the wetting and/or the adhesion of the adhesive to/on the contact surface are improved. In particular, non-polar materials, for example plastics that consist of long polymer chains (polypropylene, PE), are difficult to bond because wetting them with adhesives is difficult. Appropriate treatment turns the non-polar material into a polar substrate.

Such activation can take place, for example, by means of a plasma treatment. The reactive species present in the plasma generate radical sites on the molecular chains to which polar groups can attach. For example, when working with an air plasma, oxygen-containing groups such as hydroxyl (—OH), carbonyl (—CO) and carboxyl (—COOH) are primarily integrated into the uppermost molecular layers.

The activation and the pretreatment, for example cleaning, of the contact surfaces can advantageously be carried out in one work step by means of a plasma treatment.

In an advantageous plasma treatment of the contact surfaces, a working gas is used which is or contains oxygen. The working gas could also be air. Furthermore, the working gas could be an inert gas, for example argon gas or a gas mixture which contains an inert gas. Finally, the working gas could be a forming gas, for example a gas consisting of hydrogen and nitrogen. The plasma is preferably an atmospheric plasma or a low-pressure plasma.

For cleaning the contact surfaces, atmospheric plasma treatment is particularly well suited for cleaning, the effectiveness of the plasma treatment depending on the choice of the working gas, the degree of ionization of the plasma and the duration of the treatment.

The components are advantageously placed in a vacuum chamber in the course of a low-pressure plasma process. The vacuum preferably is at a pressure of 10 to 500 Pa.

According to a further preferred embodiment, the first and/or the second contact surface are coated with an adhesion promoter. An adhesion promoter creates a kind of bridge between the adhesive and the contact surface, which improves the adhesion. The adhesion promoter advantageously consists of dilute solutions of the adhesive bases. The adhesion promoter can advantageously be applied to the contact surfaces by rolling, spraying or dipping processes.

According to a preferred embodiment, a first tempering medium is used to temper the first component. A second tempering medium is advantageously used for tempering the second component. The first and/or the second tempering medium can preferably be a fluid, electromagnetic radiation or a plasma. A fluid can be a liquid, for example water, or a gas, for example air. A corresponding tempering device therefore advantageously brings the tempering medium onto the contact surfaces. Such tempering devices could therefore advantageously be hot air blowers or heating pumps. Furthermore, in the event that the tempering medium is electromagnetic radiation, the tempering device can be a radiant heater or infrared heater. It would also be conceivable to use a heating wire which, for example, is inserted into the preferred receiving volume. The first tempering medium is preferably supplied to the first component by a first tempering device. The second tempering medium is preferably supplied to the second component by a second tempering device.

If the second component contains a receiving volume that is limited by the second contact surface, it is advantageous if the second tempering medium is introduced into the receiving volume of the second component.

According to a preferred embodiment, the second tempering medium is introduced into the receiving volume of the second component. The at least one second contact surface can thus be tempered according to temperature $T1$. Such tempering is direct tempering. Alternatively, the second contact surface can be tempered indirectly. In the case of indirect tempering, the second tempering medium advantageously touches a tempering region of the second component, the tempering region of the second component encompassing, surrounding, or being arranged in the immediate vicinity of this contact surface. The tempering area is preferably a material portion of the second component which is delimited by the tempering surface and, at least in portions, by the second contact surface. In the case of indirect tempering, a tempering medium advantageously touches a tempering surface of the tempering region, which is a portion of an outer surface of the second component. A heat flow advantageously takes place from the tempering surface through the tempering area to the second contact surface, or from the second contact surface to the tempering surface. Depending on the direction of the heat flow, the second contact surface is heated or cooled. The second contact surface can thus be brought to temperature $T1$. In the case of heating, due to an advantageous thermal conductivity of the material in the tempering region, after the tempering medium has touched the surface and the temperature of the receiving surface has been reached, heat diffusion takes place to the second contact surface, as a result of which the temperature is brought to temperature $T1$.

According to a further embodiment, the second tempering device and an application device for the adhesive are stationarily arranged in an apparatus for connecting two components. The term "stationary" means a fixed arrangement at a certain position. The second component is preferably guided by a first transport device to a processing position by the second tempering device and/or by the application device for the adhesive. The apparatus for connecting two components advantageously further comprises a second transport device which introduces the first component into the second component or attaches it to the second component. Advantageously, the first and second transport devices guide a plurality of first and second components one after the other into the processing position, which enables series production. The application device for the adhesive is advantageously connected to an adhesive supply. The adhesive in the adhesive supply is preferably tempered by means of an adhesive tempering device.

According to a further advantageous embodiment, both the first and the second component are tempered by a single tempering device. The first component is advantageously introduced in portions into a receiving volume of the second component before the tempering is carried out.

According to a further preferred embodiment, the adhesive is cured by means of a curing device. The type of curing device depends on the type of adhesive used. For example, some adhesives cure at certain elevated temperatures. Accordingly, the curing device can preferably be a heat source, for example an infrared radiator, a hot air blower or the like. Other adhesives in turn harden due to the influence of electromagnetic radiation such as light or UV radiation. Accordingly, the curing device could be a radiation source, for example a lamp, an LED, a UV lamp, or a UV LED. The radiation source is advantageously placed outside the second component. The second component should therefore advantageously be transparent to the corresponding radiation. The apparatus for connecting two components advantageously includes the curing device, the components of the curing device preferably being fed by means of the transport device.

Other adhesives, in particular 2-component adhesives, harden at room temperature after the two components have been mixed. A corresponding curing device would therefore not be necessary.

According to a further preferred embodiment, the first component is a lancing means. The second component is preferably a syringe body. The syringe body preferably has a reservoir in which a medium provided for administration can be stored. The reservoir preferably has a proximal opening of the syringe body. It is also advantageous that the syringe body has a distal end region in which a lancing means channel is provided. The lancing means channel preferably corresponds to the receiving volume of the second component. The distal end region advantageously has a distal opening of the syringe body. The distal end region can advantageously be a syringe cone. The lancing device channel is advantageously connected to the reservoir. The syringe body preferably has a transition region which is arranged between the distal end region and the reservoir. The reservoir advantageously has a first outer diameter and a first inner diameter. The distal end region preferably has a second outer diameter and a second inner diameter. The second outer diameter is advantageously smaller than the first outer diameter and the second inner diameter is smaller than the first inner diameter. The first inner diameter advantageously merges into the second inner diameter in the transition region. The first outer diameter advantageously transitions into the second outer diameter in the transition region. The distal end region is advantageously conical.

The terms "distal" and "proximal" are to be understood such that the distal end of the syringe is closer to the application site, and the proximal end is farther away from the application site. The terms "distal and proximal direction" are to be understood analogously.

A lancing means refers to needles, cannulas and similar devices for such purposes. The lancing means advantageously consists of a metal, preferably stainless steel.

According to an advantageous embodiment, the lancing means is introduced into the lancing means channel in such a way that the proximal end of the lancing means does not protrude beyond the proximal end of the lancing means channel and into the transition region. The first contact surface advantageously extends from the proximal end of the lancing means to the length of the lancing means, out of which the lancing means protrudes from the lancing means channel.

According to a further advantageous embodiment, the lancing means is introduced into the lancing means channel in such a way that the proximal end of the lancing means protrudes beyond the proximal end of the lancing means channel and into the transition region. The contact surface of the lancing device is thus provided between two surfaces which are not wetted with adhesive.

According to a further advantageous embodiment, it is advantageous if the lancing means channel has a larger inner diameter in the distal section than in the proximal section. The lancing means is inserted and glued into this distal section. The transition region to the proximal section with the smaller diameter can serve as a contact surface for the lancing means. The diameter of the distal section is preferably in a range between 0.7 and 1.3 mm, particularly preferably approximately 1 mm. The diameter of the proximal section is preferably in a range between 0.45 mm and 0.9 mm and particularly preferably approximately 0.7 mm.

According to a further preferred embodiment, the syringe body is made of glass. The syringe body preferably consists of silicate glass, for example borosilicate glass or quartz glass. Glass syringes of this type have excellent chemical resistance, neutrality and impermeability.

According to a preferable embodiment, the syringe body is made of glass or a synthetic polymer plastic, preferably a polyolefin, for example polypropylene or polyethylene, particularly preferably a cyclic olefin polymer (COP) or a cyclic olefin copolymer (COC). COC is, in contrast to the partially crystalline polyolefins, such as polyethylene and polypropylene, amorphous and thus transparent.

According to an advantageous embodiment, the second contact surface is tempered indirectly. At least a portion of an outer surface of the distal end region is preferably tempered by means of a second tempering device, the second contact surface being tempered by means of heat diffusion from the outer surface of the distal end region to the second contact surface or from the second contact surface to the outer surface of the distal end region.

The portion of the outer surface of the distal end region thus corresponds to the tempering surface. Since the lancing means channel is generally configured as a circular cylinder, the second contact surface is the inner surface of this hollow cylinder. The distal end region is advantageously the tempering region. It is advantageous if the entire distal end region is tempered in such a way that it is at temperature T1.

It would be conceivable for the second tempering device to have an opening which is spaced in the radial direction apart from the distal end region. The tempering medium emerges from this opening and touches a portion of the outer surface of the distal end region. Due to the heat diffusion in the material of the distal end region, the latter is tempered overall.

Furthermore, it would be possible for the second tempering device to have at least two openings which are spaced apart from the distal end region in different radial directions. For example, it would be possible to arrange two such openings diametrically opposite one another. The tempering medium can thus touch two diametrically opposite portions of the distal end region. The tempering of the distal end section through the heat diffusion in its material can thus be carried out more quickly. The internal second contact surface is preferably tempered by the thermal conductivity of the material of the distal end region, which is advantageously glass or a synthetic polymer plastic. The temperature of the portion of the outer surface is advantageously monitored by a temperature measuring device. The temperature of the second contact surface can be determined by the temperature of the outer surface and by means of further material parameters such as volume and thermal conductivity.

According to a further preferred embodiment, the second contact surface is tempered directly. The second tempering medium is advantageously introduced into the lancing means channel of the distal end region by a second tempering device. The tempering device is preferably placed at a distal opening of the lancing means channel.

The second tempering medium can advantageously be a fluid or electromagnetic radiation both in direct and in indirect tempering. Preferred configurations of the second tempering device could thus be, for example, hot air blowers, radiant heaters, hot water pumps or the like.

According to a further preferred embodiment, the second tempering medium is removed from the syringe body by a discharge device, the discharge device being arranged in the transition region. The discharge device advantageously comprises a sealing device, which is sealingly arranged in a sealing manner on an inner wall of the transition region, so that no tempering medium gets into the reservoir.

Such a discharge device can be, for example, a suction device. Since media which are sensitive to contamination, for example vaccines, are stored in the reservoir, it is desirable that no tempering medium, for example fluid, plasma, etc., gets into the reservoir. This is advantageously ensured by the discharge device, which is sealingly arranged on an inner wall of the transition region by the sealing device.

According to one embodiment, a urethane methacrylate is used as the adhesive. At 25° C., such an adhesive has a viscosity of 1000 to 2000 mPa s. Advantageously, the sufficient reduction in viscosity to fill the adhesive cavity is in a temperature range between 39° C. and 46° C., preferably at 42° C. Such an advantageous adhesive could be the product LOCITINE® 3345.

Advantages are also achieved by an apparatus for connecting two components, in particular by an apparatus for fitting a syringe body with a lancing means.

This apparatus is preferably suitable and intended to carry out the described embodiments of the method (in particular individual ones and/or several thereof).

The apparatus advantageously comprises a first transport device and a second transport device in the form of a gripping tool for gripping the lancing means. Furthermore, it is advantageous if the apparatus comprises an application device for the adhesive as well as a second and/or a first tempering device. It is also advantageous if the apparatus comprises a temperature measuring device, a control device and a curing device.

Other advantages, aims and properties of the present invention are explained with reference to the following description of the attached drawings. Similar components may have the same reference signs in the various embodiments.

BRIEF DESCRIPTION OF THE DRAWINGS

Preferred and alternative examples of the present invention are described in detail below with reference to the following drawings.

DETAILED DESCRIPTION OF THE PREFERRED EMBODIMENT

FIGS. 1 to 9 show embodiments of a method for connecting a first component (1) to a second component (3). In the FIGURES and below, the first component (1) is a lancing means (2), and the second component (3) is a syringe body (4). However, this is to be understood without restricting the generality of the terms "first component (1)" and "second component (3)." The method can be applied analogously to other components. In the following, the terms "first component (1)" and "lancing means (2)" are to be understood synonymously. The terms "second component (1)" and "syringe body (2)" are also to be understood synonymously.

The method for connecting a first component (1), in particular a lancing means (2), to a second component (3), in particular a syringe body (4), in order to produce a product (5) for medical or cosmetic purposes, by means of adhesion, includes the following steps: (a) providing the first (1, 2) and the second component (3, 4); (b) tempering at least one first contact surface (6) of the first component (1, 2) and/or at least one second contact surface (7) of the second component (3, 4) to a temperature T1; and (c) applying an adhesive (8) to at least one portion of the first contact surface (6) and/or to at least one portion of the second contact surface (7), the adhesive (8) having a temperature T2, the temperatures T1 and T2 differing only by a tolerance deviation, the tolerance deviation being at most 10° C.

The temperature T2 is advantageously greater than 20° C. Temperature T1 preferably deviates from temperature T2 by at most 5° C. More preferably, temperature T1 deviates from temperature T2 by at most 4° C. More preferably, temperature T1 deviates from temperature T2 by at most 3° C. More preferably, temperature T1 deviates from temperature T2 by at most 1.5° C.

The invention accordingly provides for one or both of the adhesive partners (1, 2, 3, 4) to be heated to the same or similar temperature as the adhesive (8) used. As a result, there is no temperature compensation when the adhesive partners (1, 2, 3, 4) and the adhesive (8) meet. The adhesive (8) maintains its desired temperature and thus also the desired viscosity.

Figure 7:
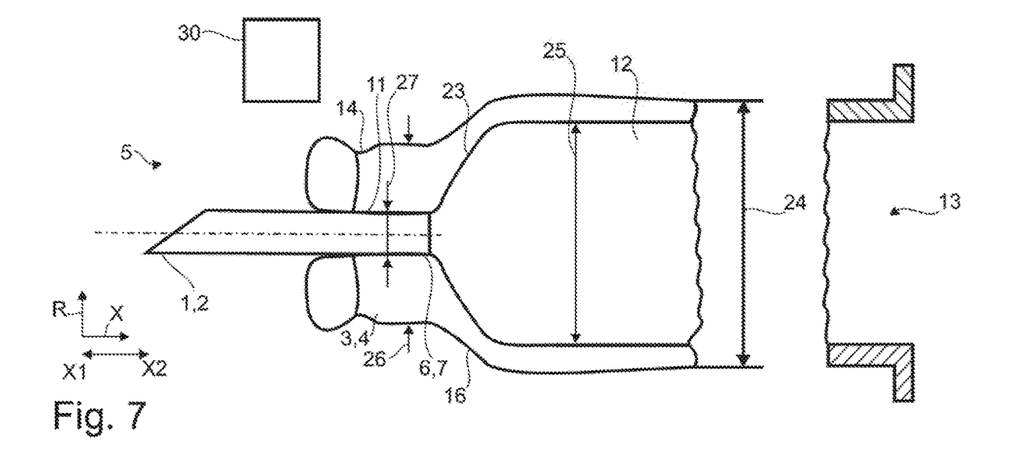
FIG. 7 shows a product produced by the method for connecting a first component, in particular a lancing means, to a second component, in particular a syringe body, according to a further embodiment.

A corresponding example product (1) produced by the method, i.e., a syringe body (4) with a lancing means (2), is shown in FIG. 7.

The syringe body (4) extends along an axial axis and has a reservoir (12) in which a medium intended for administration can be stored. The axial axis also has a distal direction X1 and a proximal direction X2.

The reservoir (12) further comprises a proximal opening (13) of the syringe body (4). The medium can be filled into the reservoir (12) through this proximal opening (18), and the plungers can then be inserted. The syringe body (4) also has a distal end region (14), in which a lancing device channel (10) is provided, the lancing device channel (10) corresponding to a receiving volume (9) of the second component (3). The distal end region (14) is also referred to as the syringe cone. The lancing means channel (10) is connected to the reservoir (12), so that a medium can enter the lancing means channel (10) from the reservoir (12).

The distal end region (14) also has a distal opening (15) of the syringe body (4). This distal opening (15) is at the same time the distal opening (15) of the lancing means channel (10). Finally, the syringe body (4) has a transition region (16) which is arranged between the distal end region (14) and the reservoir (12).

The reservoir (12) has a first outer diameter (25) and a first inner diameter (26). The distal end region (14) has a second outer diameter (26) and a second inner diameter (27). The second outer diameter (26) is smaller than the first outer diameter (24), and the second inner diameter (27) is smaller than the first inner diameter (25). In the transition region (16), the first inner diameter (25) transitions into the second inner diameter (27). Likewise, in the transition region (16), the first outer diameter (24) transitions into the second outer diameter (26).

To temper the first contact surface (6) of the first component (1) or the lancing means (2) in step (b), a first tempering medium (19) is used which is supplied to the lancing means (1, 2) by a first tempering device (17). A second tempering medium (20), which is supplied to the syringe body (3, 4) by a second tempering device (18), is used to temper the second contact surface (7) of the second component (3) or the syringe body (4). The first (19) and/or the second tempering medium (20) can be a fluid, electromagnetic radiation or a plasma. Accordingly, the first (17) and/or the second tempering device (18) could be a hot air blower, a radiant heater, a hot water pump or the like.

The tempering in step (b) can take place directly or indirectly. In the case of direct tempering, a tempering medium (19, 20) touches the at least one first contact surface (6) and/or the at least one second contact surface (7). In the case of indirect tempering, a tempering medium touches a tempering area (1a, 3a) of the first component (1) and/or second component (3), in which case the tempering area (1a, 3a) of the first component (1) and/or second component (3a) comprises or surrounds the contact surface (6, 7) of the respective component (1, 3), or is arranged in the immediate vicinity of this contact surface (6, 7). In the case of indirect tempering, a tempering medium (19, 20) touches a tempering surface (3b, 4b) of the tempering area (3a, 4a) which does not correspond to the contact surface. Heat flow advantageously takes place from the tempering surface (3b, 4b) through the tempering area (3a, 4a) to the corresponding contact surface (6, 7) or heat flow from the corresponding contact surface (6, 7) to the tempering surface (3a, 4a). The direction of the heat flow determines whether the corresponding contact surface (6, 7) is heated or cooled.

Figure 1:
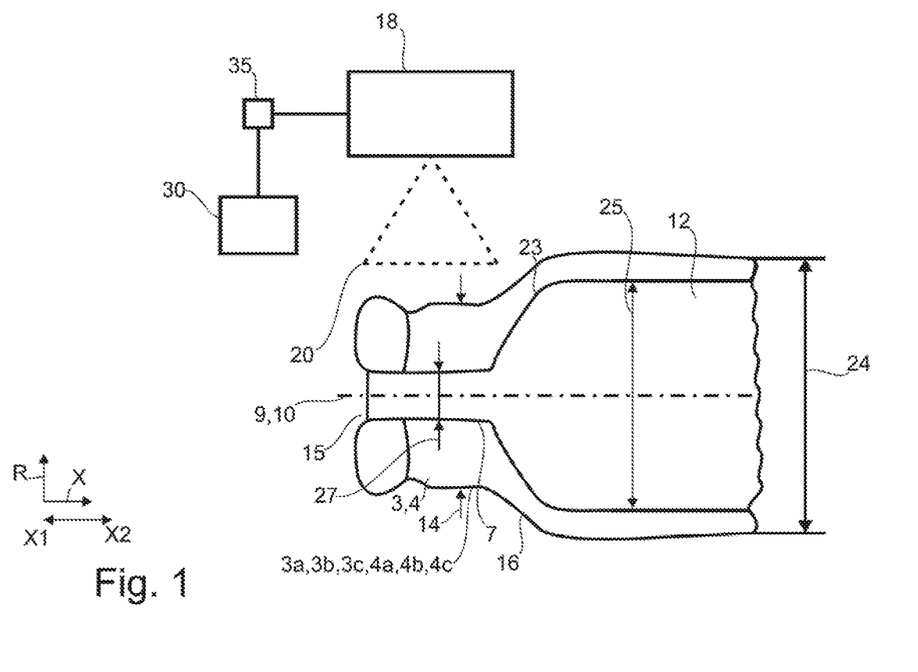
FIG. 1 shows a preferred section of a method for connecting a first component, in particular a lancing means, to a second component, in particular a syringe body, according to one embodiment.
Figure 8:
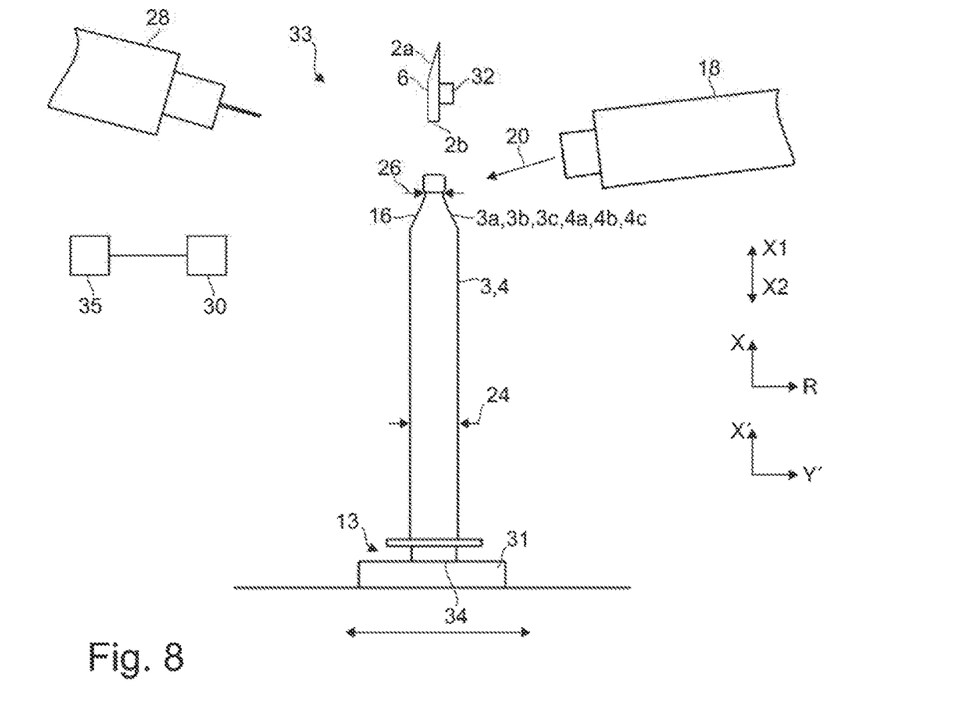
FIG. 8 shows a preferred section of a method for connecting a first component, in particular a lancing means, to a second component, in particular a syringe body, according to a further embodiment.

In the embodiments according to FIGS. 1 and 8, the second contact surface (7) is indirectly tempered, at least a portion of an outer surface (3a, 4a) of the distal end region (14) being tempered by means of a second tempering device (18), the tempering being carried out by means of heat diffusion from the outer surface (3a, 4a) of the distal end region (14) to the second contact surface (7) or from the second contact surface (7) to the outer surface (3a, 4a) of the distal end region (14) the second contact surface (7).

The portion of the outer surface (3c, 4c) of the distal end region (14) thus corresponds to the tempering surface (3b, 4b). Since the lancing means channel (10) is designed as a circular cylinder, the second contact surface (7) is the inner surface of this hollow cylinder. The distal end region (14) is advantageously the tempering region. It is advantageous if the entire distal end region (14) is tempered in such a way that it is at temperature T1.

Figure 9:
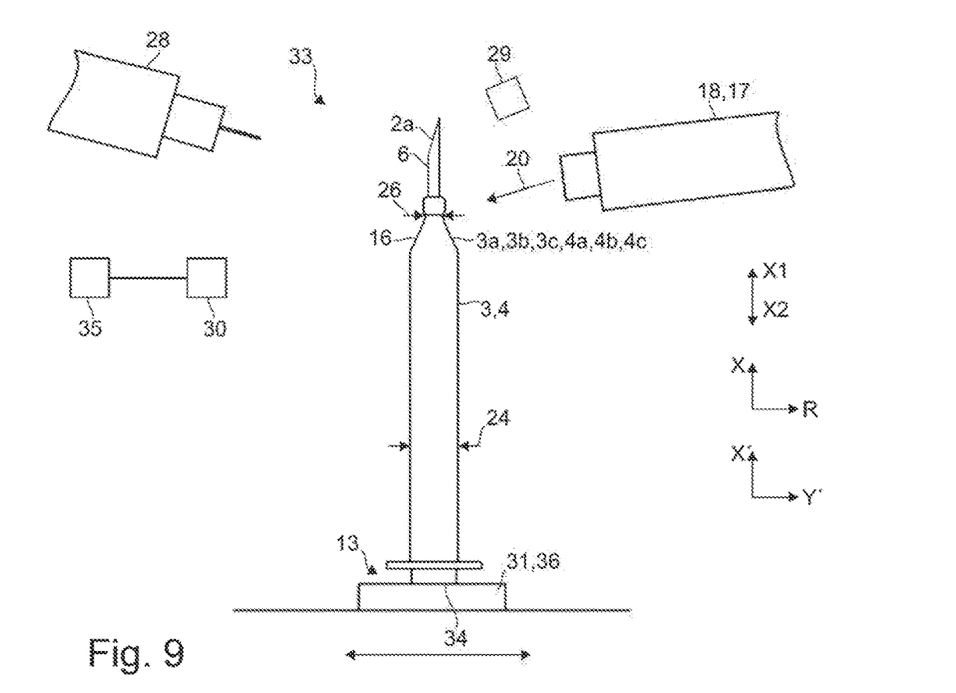
FIG. 9 shows a preferred portion of a method for connecting a first component, in particular a lancing means, to a second component, in particular a syringe body, according to another embodiment.

A further embodiment of the indirect tempering is shown in FIG. 9. The first component (1), i.e., the lancing means (2) is inserted into the receiving volume (9) or the lancing means channel (10) before the tempering in step (b). At least one portion of an outer surface (3a, 4a) of the distal end region (14) is tempered by the tempering device (17, 18) analogously to the embodiment of FIG. 8. Since the lancing means (2) is already in the lancing means channel (10), the first contact surface (6) of the lancing means (2) is also tempered by the heat diffusion from or to the outer surface (3a, 4a).

Alternatively or cumulatively, the tempering medium (19, 20) can touch a portion of the lancing means (2) which projects beyond the distal opening (15) of the syringe body. This portion would then be the tempering area (1a) of the first component (1). The first (6) and/or the second contact surface (7) is then tempered by the heat diffusion from or to this tempering region (1a).

The tempering device (17, 18) has an opening which is spaced in the radial direction apart from the distal end region (14) and/or the lancing means (2). The tempering medium (19, 20) emerges from this opening and touches the respective outer surface of the tempering area (1a, 3a, 4a).

It would also be possible for the tempering device (17, 18) to have at least two openings which are spaced in different radial directions apart from the distal end region (14) and/or the lancing means (2). For example, it would be possible to arrange two such openings diametrically opposite one another. The tempering medium can thus touch two diametrically opposite portions of the distal end region (14) and/or the lancing means (2).

Figure 2:
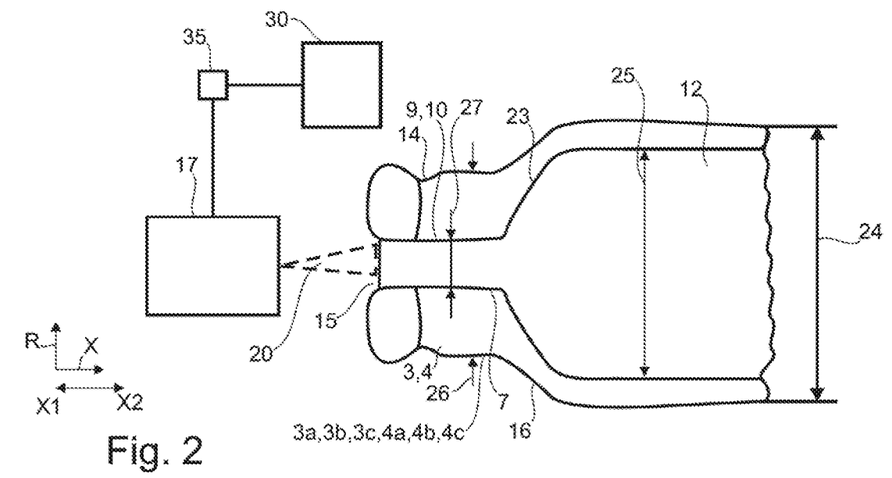
FIG. 2 shows a preferred section of a method for connecting a first component, in particular a lancing means, to a second component, in particular a syringe body, according to a further embodiment.
Figure 3:
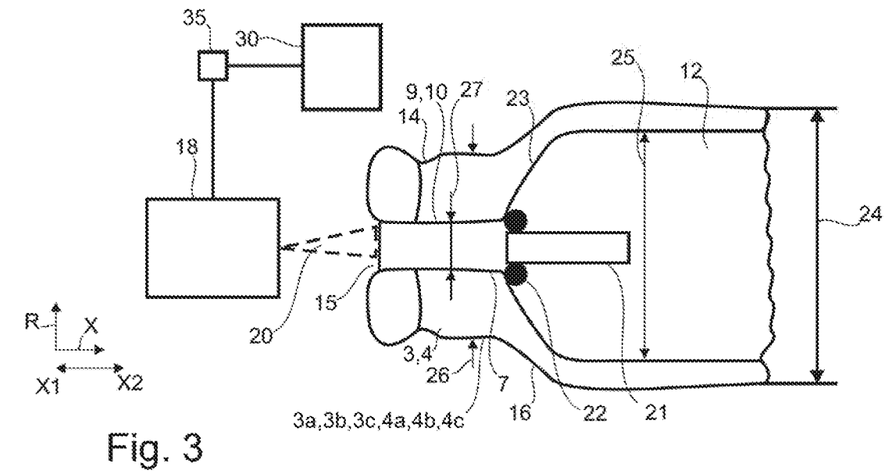
FIG. 3 shows a preferred section of a method for connecting a first component, in particular a lancing means, to a second component, in particular a syringe body, according to a further embodiment.
Figure 4:
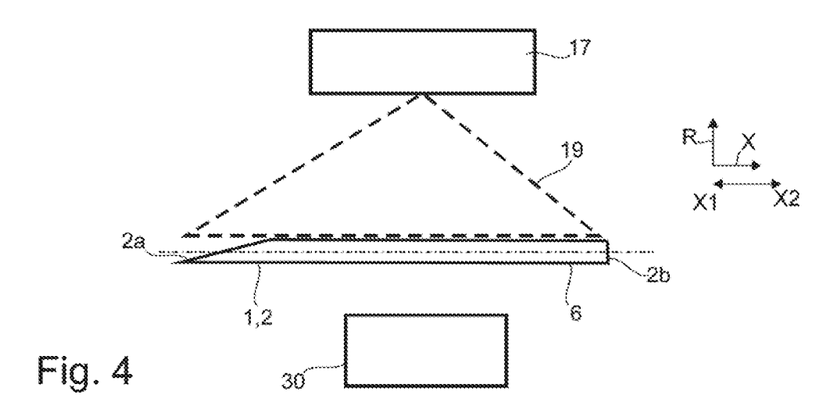
FIG. 4 shows a preferred section of a method for connecting a first component, in particular a lancing means, to a second component, in particular a syringe body, according to a further embodiment.

According to the embodiments as per FIGS. 2, 3 and 4, the contact surfaces (6, 7) are directly tempered.

For example, FIG. 4 shows a direct tempering of the first contact surface (6) of the first component (1) or of the lancing means (2). The tempering medium (19) is applied by the first tempering device (17) directly to the first contact surface.

FIGS. 2 and 3 show a direct tempering of the second contact surface (7) of the second component (3) or of the syringe body (4), in particular of the distal end section (14). According to this embodiment, a second tempering medium (20) is introduced into the lancing means channel (10) of the syringe body (4) through the second tempering device (18). Such a tempering device (18) can be any suitable device which can introduce a suitable tempering medium (20) into the lancing device channel (10). The second tempering device (18), or an outlet opening of the second tempering device, is placed at a distal opening (15) of the lancing means channel (10) so that the tempering medium (20) penetrates into the lancing means channel (9, 10) in the proximal direction X2. There it then touches the second contact surface (7) directly, thereby tempering it.

Due to the high purity requirements for syringe bodies, it is often desirable that the tempering medium (19, 20) does not get into the reservoir (12) of the syringe body (4). Accordingly, in the case of direct tempering of the syringe body (4), a discharge device (21) can be provided which removes the second tempering medium (20) from the syringe body (4). Such a discharge device (21) is shown schematically in FIG. 3 and can be a suction device. The discharge device (21) is equipped with a sealing device (22) which is sealingly arranged on an inner wall (23) of the transition region (16). The discharge device (21) and the sealing device (22) prevent a tempering medium (19, 20) from getting into the reservoir (12). The discharge device (21) is inserted through the proximal opening (13) of the syringe body (3, 4). It would also be conceivable for the discharge device (21) to be arranged in the first transport device (31) which transports the second component (3) or the syringe body.

For both direct and indirect tempering, only the lancing means or only the syringe body can be tempered. It would also be possible for the lancing means (1, 2) and the syringe body (3, 4) to be tempered by one or more tempering devices (17, 18).

Figure 5:
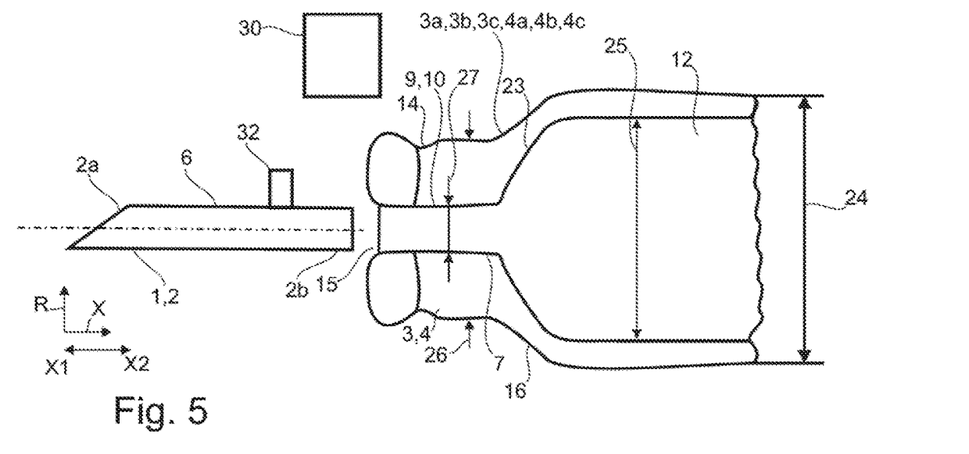
FIG. 5 shows a preferred section of a method for connecting a first component, in particular a lancing means, to a second component, in particular a syringe body, according to a further embodiment.
Figure 6:
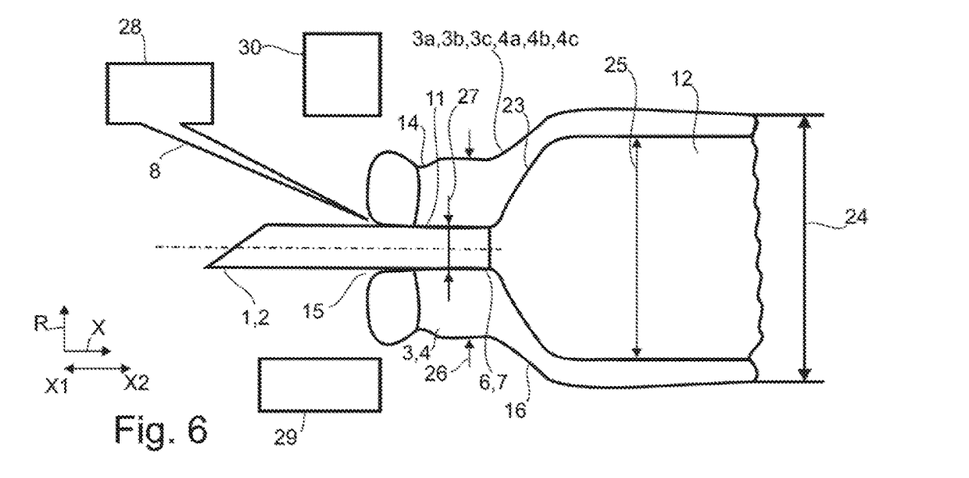
FIG. 6 shows a preferred section of a method for connecting a first component, in particular a lancing means, to a second component, in particular a syringe body, according to a further embodiment.

After step (b), i.e., tempering at least one first contact surface (6) of the first component (1, 2) and/or at least one second contact surface (7) of the second component (3, 4) to a temperature T1, the lancing means is advantageously (1, 2) introduced into the lancing means channel (9, 10) of the syringe body (3, 4) at least in portions. The lancing means (2) has a proximal end (2b) and a distal end (2a), which is provided with a cut. The proximal end (2b) of the lancing device (1, 2) is introduced into the lancing means channel (9, 10) in the proximal direction X2. A certain portion of the lancing means having the distal end (2a) therefore projects beyond the distal opening (15) of the syringe body (4). This is shown in FIGS. 5 to 6. In this embodiment, the proximal end (2b) of the lancing means (1, 2) does not protrude in the proximal direction (X2) beyond the lancing means channel (9, 10). However, it would also be possible for the lancing means to be introduced into the syringe body in such a way that the proximal end (2b) of the lancing means (1, 2) projects into the transition region (16).

The adhesive cavity (11) is therefore formed by the remaining volume of the lancing means channel (9, 10) which is not filled by the lancing means (1, 2).

In step (c), the adhesive (8) is then applied to the entire first contact surface (6) and the entire second contact surface (7). This is done by filling the adhesive cavity (11) with adhesive (8). This is shown in FIG. 6. The adhesive (8) is introduced through an application device (28) through the distal opening of the syringe body (4) into the lancing means channel (9, 10) or the adhesive cavity (11), so that the adhesive cavity (11) is completely filled with adhesive (8), and all of the contact surfaces (6, 7) are covered with adhesive. After the adhesive has cured, there is thus an adhesive connection between the entire first contact surface (6) and the entire second contact surface (7).

Alternatively, after step (c), i.e., applying an adhesive (8) to at least one portion of the first contact surface (6) and/or to at least one portion of the second contact surface (7), the lancing means (1, 2) is introduced into the lancing means channel (9, 10) at least in portions. The lancing means (1, 2) is inserted into the lancing means channel (9, 10) in the proximal direction X2. This is shown in FIG. 5. In step (c), the adhesive (8) is previously applied to at least one portion of the first contact surface (6) and/or to at least one portion of the second contact surface (7). The amount of adhesive (8) applied is measured such that the adhesive cavity (11) is filled when the lancing means has been introduced into the lancing means channel (9, 10).

It would be conceivable to provide a temperature measuring device (30) which monitors temperature T1 and/or temperature T2. Such a temperature measurement could be carried out contactlessly or with a temperature sensor. It would be conceivable to measure only the temperature of an outer surface of the distal end region (14). The dimensions of the distal end region (14) and the specification of the material can then be used to infer the temperature T1 of the second contact surface. The temperature measuring device (30) can be connected to a control device (35) which compares the measured value with the predetermined target value. The control device (35) can then control the tempering devices (17, 18) accordingly.

Optionally, the first contact surface (6) can be pretreated and/or activated before step (c), this pretreatment of the first contact surface (6) being selected from the group including cleaning, mechanical pretreatment, chemical pretreatment, thermal pretreatment, electrochemical pretreatment, and physical pretreatment. The second contact surface (7) can also be pretreated and/or activated before step (c), the pretreatment of the second contact surface (7) being selected from the group including cleaning, mechanical pretreatment, chemical pretreatment, thermal pretreatment, electrochemical pretreatment, and physical pretreatment.

The adhesive (8) can be cured by a suitable curing device (29). The curing device is arranged in the radial direction (R) next to the distal end region (14).

An apparatus (33) for connecting two components, in particular an apparatus (33) for fitting a syringe body (4) with a lancing means (6), is also shown in the drawings, in particular in FIG. 8. This apparatus (33) comprises the vertical axis X', which is preferably parallel to the axial axis X of the syringe body (4). The apparatus further comprises a horizontal axis Y'.

The apparatus (33) comprises a first transport device (31) which feeds the syringe body (4) to a processing position. The transport device comprises a receiving device (34) in which the proximal end of the syringe body (4) is received. The apparatus (33) further comprises an application device (28) for the adhesive (8). This application device is connected to an adhesive supply. The application device preferably comprises an adhesive tempering device, by means of which the temperature T2 of the adhesive (8) can be adjusted. This adhesive tempering device can be integrated into the adhesive supply. Alternatively, the amount of adhesive removed can be tempered. It is also conceivable for a temperature measuring device to be provided which measures the temperature of the adhesive. This temperature measuring device can also be connected to the control device (35), which compares the adhesive temperature with the predetermined value and controls the adhesive tempering device accordingly.

The apparatus (33) comprises a first and/or a second tempering device, the temperature measuring device (30), the control device, and a curing device (29). The apparatus (33) further comprises a second transport device (32) in the form of a gripping tool for gripping the lancing means (6). The lancing means (6) can advantageously be inserted into the lancing means channel (10) of the syringe body (4) by means of the gripping tool (32).

The syringe body (4) and/or the lancing means (2) is placed in the processing position in such a way that the tempering device(s) (17, 18) and the application device (28) for the adhesive (8), optionally the curing device (29), can perform their function accordingly. For example, it would be conceivable for the tempering device (s) (17, 18), the application device (28) for the adhesive (8) and, if appropriate, the curing device (29) to be arranged radially around a processing position. Alternatively, it would be conceivable for the syringe body (4) and/or the lancing means (2) to be guided to a certain device (17, 18, 28, 29) one after the other. Thus, a processing position would exist for each of the devices mentioned.

All the features disclosed in the application documents are claimed as being essential to the invention, provided that, individually or in combination, they are novel over the prior art.

LIST OF REFERENCE SIGNS

1 First component
1a Tempering region of the first component
2 Lancing means
2a Distal end of the lancing means
2b Proximal end of the lancing means
3 Second component
3a Tempering region of the second component
3b Tempering surface
3c Outer surface of the second component
4 Syringe body
4a Tempering region of the syringe body
4b Tempering surface
4c Outer surface of the syringe body
5 Product
6 First contact surface of the first component
7 Second contact surface of the second component
8 Adhesive
9 Receiving volume 10 Lancing means channel
11 Adhesive cavity
12 Reservoir
13 Proximal opening of the syringe body
14 Distal end region of the syringe body
15 Distal opening of the syringe body
16 Transition region of the syringe body
17 First tempering device
18 Second tempering device
19 First tempering medium
20 Second tempering medium
21 Discharge device
22 Sealing device
23 Inner wall of the transition region
24 First outer diameter of the reservoir
25 First inner diameter of the reservoir
26 Second outer diameter of the distal end region
27 Second inner diameter of the distal end region
28 Application device
29 Curing device
30 Temperature measuring device
31 First transport device
32 Second transport device
33 Apparatus for connecting two components
34 Receiving device
35 Control device
X Axial axis
$X_1$ Distal direction
$X_2$ Proximal direction
R Radial direction
X' Vertical axis of the apparatus for connecting two components
Y' Horizontal axis of the apparatus for connecting two components While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. A method for connecting a first component, in the form of a lancing means, to a second component, in the form of a syringe body, in order to produce a product for medical or cosmetic purposes, by means of adhesion, comprising the following steps:
   (a) Providing the first and the second component, wherein the first and the second components are at a room temperature of approximately 20° C.;
   (b) Changing the temperature of at least one first contact surface of the first component and at least one second contact surface of the second component to a temperature T1; and
   (c) After step (b), applying an adhesive to at least one portion of the first contact surface and/or to at least one portion of the second contact surface, wherein the adhesive is at a temperature T2, wherein temperatures T1 and T2 only differ by a tolerance deviation, wherein the tolerance deviation is at most 3° C., wherein temperature T2 is larger than 25 degrees C., wherein the adhesive is a viscous organic adhesive, wherein the adhesive has a required viscosity at temperature T2, and an impairment of the required viscosity of the adhesive is excluded, due to the difference of the temperatures T1 and T2 only by a tolerance deviation, wherein the adhesive is urethane methacrylate, wherein at 25° C., such an adhesive has a viscosity of 1000 to 2000 mPa s, wherein a sufficient reduction in viscosity requires a temperature range between 39° C. and 46° C.

2. The method according to claim 1, wherein changing the temperature in step (b) can take place directly or indirectly, wherein, in the case of changing the temperature directly, a tempering medium directly touches the at least one first contact surface and/or at least one second contact surface, wherein, in the case of changing the temperature indirectly, a tempering medium touches a tempering region of the first component and/or second component, wherein the tempering region of the first component and/or the second component comprises or surrounds the contact surface of the respective component or is arranged in the immediate vicinity of this contact surface.

3. The method according to claim 1, wherein the second component has a receiving volume, which is limited, at least in portions, by the second contact surface, wherein the first component is arranged in portions within the receiving volume, wherein, given an arrangement of the first component within the receiving volume, the first and the second contact surface are opposite each other, wherein, given an arrangement of the first component within the receiving volume at least in portions between the contact surfaces, an adhesive cavity is formed.

4. The method according to claim 3, wherein after step (b), the first component is introduced into the receiving volume of the second component at least in portions, wherein, in step (c), the adhesive is applied to the entire first contact surface and the entire second contact surface by filling the adhesive cavity with adhesive.

5. The method according to claim 3, wherein after step (c), the first component is introduced into the receiving volume of the second component at least in portions, wherein, in step (c), the adhesive is applied to at least one portion of the first contact surface or to at least one portion of the second contact surface, wherein the amount of adhesive applied is measured such that the adhesive cavity is filled.

6. The method according to claim 3, wherein the syringe body has a reservoir in which a medium provided for administration can be stored, wherein the reservoir has a proximal opening of the syringe body, wherein the syringe body has a distal end region, in which a lancing means channel is provided, wherein the lancing means channel corresponds to the receiving volume of the second component, wherein the distal end region has a distal opening of the syringe body, wherein the syringe body has a transition region, which is arranged between the distal end region and the reservoir.

7. The method according to claim 6, wherein the temperature of the second contact surface is changed indirectly, wherein the temperature of at least a portion of an outer surface of the distal end region is changed by means of a second tempering device, wherein the temperature of the second contact surface is changed by means of thermal diffusion from the outer surface of the distal end region to the second contact surface, or from the second contact surface to the outer surface of the distal end region.

8. The method according to claim 6, wherein the temperature of the second contact surface is changed directly, wherein a second tempering medium is introduced by a second tempering device into the lancing means channel of the distal end region, wherein the tempering device is placed at a distal opening of the lancing means channel, wherein the second tempering medium is removed from the syringe body by a discharge device, wherein the discharge device is arranged in the transition region, wherein the discharge device comprises a sealing device which is sealingly arranged on an inner wall of the transition region, so that no tempering medium gets into the reservoir.

9. The method according to claim 1, wherein in step (b) the at least one first contact surface of the first component and at least one second contact surface of the second component are heated to the temperature T1, wherein without the change of temperature according to step (b), the temperature compensation upon contact of the adhesive with the contact surfaces would accordingly decrease the adhesive temperature T2, as a result of which the viscosity of the adhesive increases.

10. The method according to claim 1, wherein the first contact surface is pretreated before step (c), wherein this pretreatment of the first contact surface is selected from the group including cleaning, mechanical pretreatment, chemical pretreatment, thermal pretreatment, electrochemical pretreatment, physical pretreatment, wherein the second contact surface is pretreated before step (c), wherein the pretreatment of the second contact surface is selected from the group including cleaning, mechanical pretreatment, chemical pretreatment, thermal pretreatment, electrochemical pretreatment, physical pretreatment.

11. The method according to claim 1, wherein a first tempering medium is used for changing the temperature of the first component, wherein a second tempering medium is used for changing the temperature of the second component, wherein the first and/or the second tempering medium can be a fluid or electromagnetic radiation, wherein the first tempering medium is supplied to the first component by a first tempering device, wherein the second tempering medium is supplied to the second component by a second tempering device.

12. The method according to claim 11, wherein the second tempering device and an application device for the adhesive are stationarily arranged in an apparatus for connecting two components, wherein the second component is guided by a first transport device to a processing position of the second tempering device and/or of the application device for the adhesive, wherein a second transport device introduces the first component into the second component or attaches the same to the second component.

\* \* \* \* \*